(12) United States Patent
Fanara et al.

(10) Patent No.: US 10,172,805 B2
(45) Date of Patent: *Jan. 8, 2019

(54) PROLONGED RELEASE FORMULATIONS COMPRISING AN 2-OXO-1-PYRROLIDINE DERIVATIVE

(75) Inventors: Domenico Fanara, Brussels (BE); Frédéric Eeckman, Brussels (BE); Monique Berwaer, Brussels (BE)

(73) Assignee: UCB BIOPHARMA SPRL, Brussels (BE)

( * ) Notice: Subject to any disclaimer, the term of this patent is extended or adjusted under 35 U.S.C. 154(b) by 197 days.

This patent is subject to a terminal disclaimer.

(21) Appl. No.: 13/129,114

(22) PCT Filed: Nov. 17, 2009

(86) PCT No.: PCT/EP2009/065271
§ 371 (c)(1),
(2), (4) Date: Jun. 24, 2011

(87) PCT Pub. No.: WO2010/057870
PCT Pub. Date: May 27, 2010

(65) Prior Publication Data
US 2011/0250282 A1 Oct. 13, 2011

(30) Foreign Application Priority Data

Nov. 18, 2008 (EP) .................................... 08105817
Jun. 2, 2009 (EP) .................................... 09100312

(51) Int. Cl.
| | |
|---|---|
| *A61K 9/16* | (2006.01) |
| *A61P 25/08* | (2006.01) |
| *A61K 31/4015* | (2006.01) |
| *A61K 9/50* | (2006.01) |
| *A61K 47/32* | (2006.01) |
| *A61K 47/38* | (2006.01) |
| *C07D 207/27* | (2006.01) |

(52) U.S. Cl.
CPC ............. *A61K 9/5078* (2013.01); *A61K 9/16* (2013.01); *A61K 31/4015* (2013.01); *A61K 47/32* (2013.01); *A61K 47/38* (2013.01); *C07D 207/27* (2013.01)

(58) Field of Classification Search
USPC ........................................................ 514/424
See application file for complete search history.

(56) References Cited

U.S. PATENT DOCUMENTS

| | | | |
|---|---|---|---|
| 4,828,840 A | | 5/1989 | Sakamoto et al. |
| 5,137,733 A | * | 8/1992 | Noda .................. A61K 9/2846 424/490 |
| 5,505,983 A | | 4/1996 | Kamada et al. |
| 5,622,716 A | | 4/1997 | Barth |
| 5,997,905 A | | 12/1999 | McTeigue et al. |
| 6,436,438 B1 | | 8/2002 | Momberger et al. |
| 6,919,373 B1 | * | 7/2005 | Lam et al. ..................... 514/532 |
| 2006/0121114 A1 | | 6/2006 | Antarkar et al. |
| 2006/0269605 A1 | | 11/2006 | Lizio et al. |
| 2007/0264346 A1 | | 11/2007 | Guimberteau et al. |
| 2007/0298098 A1 | | 12/2007 | Jenkins et al. |
| 2008/0026051 A1 | * | 1/2008 | Lizio ................... A61K 9/5015 424/452 |
| 2008/0193543 A1 | * | 8/2008 | Morello, III ......... A61K 9/0009 424/490 |

FOREIGN PATENT DOCUMENTS

| | | |
|---|---|---|
| CA | 2016039 C | 11/1990 |
| CA | 1312548 C | 1/1993 |
| EP | 1558223 A2 * | 8/2005 |
| EP | 1699439 A2 * | 9/2006 |
| JP | 10-182438 A | 7/1998 |
| WO | WO 0162726 A2 * | 8/2001 |
| WO | WO 2005060939 A2 * | 7/2005 |
| WO | 06/088864 A | 8/2006 |
| WO | 06/102964 A | 10/2006 |
| WO | WO 2006102964 A2 * | 10/2006 |
| WO | 2007/093642 A2 | 8/2007 |
| WO | 2007/141002 A1 | 12/2007 |
| WO | 08/027993 A | 3/2008 |
| WO | WO 2008027993 A2 * | 3/2008 |
| WO | 09/036811 A | 3/2009 |

OTHER PUBLICATIONS

Cellets (<URL:http:/www.cellets.org/download/cellets.org/download/cellets_english.pdf.) date published Sep. 17, 2008.*
An Investigation of Formulation Factors and Processing Parameters for the Powder-Coating of Tablets Dorothea Sauer, PhD. The University of Texas at Austin, 2008.*
Sauer (Sauer, Dissertation, Univ. of Texas at Austin, May 2008).*
Cellets (See accessed at URL:http:/www.cellets.org/download/cellets.org/download/cellets_english.pdf)[online] Publ. Sep. 17, 2008).*
International Preliminary Report on Patentability issued in corresponding application PCT/EP2009/065271 dated May 24, 2011; 7 sheets.
Kalantzi et al., "Recent Advances in Oral Pulsatile Drug Delivery," Recent Patents on Drug Delivery & Formulation, 2009, vol. 3, No. 1, pp. 49-63.
Sharma et al., "Recent trends in pulsatile drug delivery systems—A review," International Journal of Drug Delivery 2 (2010) 200-212.
Evonlik Industries Eudragit Product Brochure 2017.

* cited by examiner

*Primary Examiner* — Bethany P Barham
*Assistant Examiner* — Dominic Lazaro
(74) *Attorney, Agent, or Firm* — McDonnell Boehnen Hulbert & Berghoff LLP

(57) ABSTRACT

The present invention relates to a pharmaceutical composition comprising Levetiracetam, Brivaracetam or Seletracetam as active ingredient, the invention relates specifically to a prolonged release formulation.

23 Claims, No Drawings

PROLONGED RELEASE FORMULATIONS COMPRISING AN 2-OXO-1-PYRROLIDINE DERIVATIVE

This application is a US national phase of International Application No. PCT/EP2009/065271 filed on Nov. 17, 2009, the disclosure of which is incorporated herein by reference in its entirety.

The present invention concerns a pharmaceutical oral composition of 2-oxo-1-pyrrolodine derivatives, a process of the preparation thereof and therapeutic uses thereof.

(S)-(−)α-ethyl-2-oxo-1-pyrrolidineacetamide, is also known and hereinafter referred to as Levetiracetam. The use of Levetiracetam, as a protective agent for the treatment and prevention of hypoxic and ischaemic type aggressions of the central nervous system (CNS) is described in European patent EP-B-0 162 036. The compound can also be employed in the treatment of epilepsy, a therapeutic indication for which it has been demonstrated that its dextrorotatory enantiomer, (R)-(+)-α-ethyl-2-oxo-1- pyrrolidine-acetamide, is completely devoid of activity (A. J. GOWER et al., Eur. J. Pharmacol., 222, (1992), 193-203).

International patent application having publication number WO 01/62726 discloses 2-oxo-1- pyrrolidine derivatives and methods for their preparation. It particularly discloses compound (2S)-2-[(4R)-2-oxo-4-propyl-pyrrolidin-1-yl] butanamide known under the international non propriety name of Brivaracetam.

International patent application having publication number WO 2005/121082 describes a process of preparation of 2-oxo-1-pyrrolidine derivatives and particularly discloses a process of preparation of (2S)-2-[(4S)-4-(2,2-difluorovinyl)-2-oxo-pyrrolidin-1-yl]butanamide known under the international non propriety name of Seletracetam.

2-oxo-1-pyrrolidine derivatives are therefore particularly useful in the pharmaceutical industry.

Brivaracetam is effective in the treatment of epilepsy. A clinical trial evaluated the efficacy and safety of Brivaracetam (5, 20 and 50 mg per day) in the adjunctive treatment of adult patients with refractory partial onset seizures, with or without secondary generalization. Brivaracetam is also effective in the treatment of patients with post-herpetic neuralgia.

Seletracetam is effective in the treatment of epilepsy. Two studies were conducted with Seletracetam in epilepsy evaluating the efficacy and safety of Seletracetam in the adjunctive treatment of partial onset seizures in highly refractory adult patients currently receiving up to three concomitant anti-epileptic drugs.

A prolonged release formulation would be particularly desirable for administration in some patients. A prolonged release formulation could be advantageously used in order to reduce the difference between plasmatic $C_{max}$ and $C_{min}$ and consequently to lower sides effects. Moreover, a prolonged release formulation improves the patient's compliance as the administration frequency could be reduced.

A same formulation which can be easily adapted for various dosages of active ingredient would be also desirable.

Moreover, a formulation easily ingested would be particularly desirable for administration in children and also in some elderly adult patients.

A prolonged release formulation once a day, would be particularly desirable.

International patent application WO 2006/088864 and US application US 2007/298098 disclose controlled release compositions which deliver Levetiracetam in a pulsatile manner, comprising a first component comprising a first population of Levetiracetam particles and a second component comprising a subsequent population of Levetiracetam particles coated with a modified release coating.

It has now surprisingly been found that sustained release behaviour could be obtained from sufficiently small size pellets and an accurate control of the release could be obtained thanks to the use of a controlled release coating.

One of the objectives of the invention is a pharmaceutical composition which can be administered orally to control the release of pharmaceutically active substances so that it can be administered in a few daily doses, ideally in a single daily dose and so to provide a therapeutic effect for at least 16 hours when administered to a patient.

Considering Levetiracetam, Brivaracetam and Seletracetam are classified as BCS I, in order to achieve a prolonged therapeutic plasmatic drug level the resulting in vitro dissolution (USP<711> apparatus n°2) in a buffered aqueous media has to show a drug release of no more than 40% after 1 hour of dissolution, of 25% -80% after 4 hours of dissolution and of no less than 80% after 16 hours of dissolution. Preferably, a profile of no more than 35% after 1 hour of dissolution, of 35% -75% after 4 hours of dissolution and of no less than 80% after 16 hours of dissolution. More preferably a profile of no more than 30% after 1 hour of dissolution, of 45% -70% after 4 hours of dissolution and of no less than 80% after 16 hours of dissolution.

However, as Levetiracetam, Brivaracetam and Seletracetam have a very high water solubility (their solubility exceeds 500 mg/ml), it is therefore not obvious to slow down their release to such an extent, above all when non-monolithic forms are used, as the total surface area is consequently dramatically increased.

Accordingly, the present invention relates to a pharmaceutical composition comprising a granulate containing an inert core which is coated by a first layer comprising an active ingredient and at least one excipient, this first layer being coated by a second layer which is a controlled release layer, and the active ingredient being an 2-oxo-1-pyrrolidine derivative of formula (I),

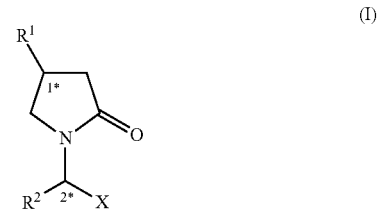

wherein,
$R^1$ is H, $C_{1-10}$ alkyl or $C_{2-6}$ alkenyl;
$R^2$ is $C_{1-10}$ alkyl or $C_{2-6}$ alkenyl;
X is —$CONR^4R^5$, —COOH, —$COOR^3$ or —CN;
$R^3$ is $C_{1-10}$ alkyl;
$R^4$ is hydrogen or $C_{1-10}$ alkyl;
$R^5$ is hydrogen or $C_{1-10}$ alkyl.

The term "active ingredient" as used herein is defined as a substance or a drug which has a therapeutic effect. It can also be a mixture of substances having a therapeutic effect.

The amount of the active ingredient present in the pharmaceutical composition of the invention may vary depending on the patient to which the compositions are administered and the disease to be treated.

The term "alkyl", as used herein, is a group which represents saturated, monovalent hydrocarbon radicals having straight (unbranched), branched or cyclic moieties, or combinations thereof. Preferred alkyl comprises 1 to 10 carbons. More preferred alkyl comprises 1 to 4 carbons. Optionally, alkyl groups may be substituted by 1 to 5 substituents independently selected from the group consisting of halogen, hydroxy, alkoxy, ester, acyl, cyano, acyloxy, acid, amide or amino group. Preferred alkyl groups are methyl, ethyl, n-propyl, trifluoromethyl and trifluoroethyl.

The term "alkenyl" as used herein represents unsubstituted or substituted branched, unbranched or cyclic hydrocarbon radicals or combinations thereof having at least one double bond. Preferred alkenyl comprises 2 to 6 carbons. More preferred alkenyl comprises 2 to 4 carbons. "Alkenyl" moieties may be optionally substituted by 1 to 5 substituents independently selected from the group consisting of halogen, hydroxy, alkoxy, ester, acyl, cyano, acyloxy, carboxylic acid, amide or amino group.

The term "halogen", as used herein, represents an atom of fluorine, chlorine, bromine, or iodine.

The term "hydroxy", as used herein, represents a group of formula —OH.

The term "alkoxy", as used herein, represents a group of formula —$OR^a$ wherein $R^a$ is $C_{1-4}$ alkyl as defined above.

The term "acyl" as used herein, represents a group of formula $R^bCO$—, wherein $R^b$ represents a $C_{1-4}$ alkyl as defined above.

The term "ester", as used herein, represents a group of formula —$COOR^C$ wherein $R^C$ represents a $C_{1-4}$ alkyl as defined above.

The term "cyano" as used herein represents a group of formula —CN.

The term "acyloxy" as used herein represents a group of formula —O—$COR^d$, wherein $R^d$ is a $C_{1-4}$ alkyl as defined above or an aryl group.

The term "aryl" as used herein, represents an organic radical derived from an aromatic hydrocarbon by removal of one hydrogen, for example a phenyl.

The term "carboxylic acid" as used herein represents a group of formula —COOH.

The term "amino group", as used herein, represents a group of formula —$NH_2$, $NHR^e$ or $NR^fR^e$ wherein $R^e$ and $R^f$ are alkyl groups as defined above in the specification.

The term "amide", as used herein, refers to a group of formula —CO—$NH_2$, —CO—$NHR^e$ or —CO—$NR^gR^h$, wherein $R^g$ and $R^h$ are alkyl groups as defined above in the specification.

The term "sulfonate group" as used herein represents a group of formula —O—$SO_2$—$R^i$ wherein $R^i$ is an alkyl or an aryl as defined here above in the specification. Preferred sulfonate groups are methanesulfonate, para-toluenesulfonate group or trifluoromethanesulfonate.

Compounds of formula (I) have at least two stereogenic centers in their structure which are indicated by (1*) and (2*). These stereogenic centers may be present in a R or S configuration, said R and S notation being used in accordance with the rules described in Pure. Appl. Chem., 45 (1976)11-30.

In one embodiment, according to first aspect of the present invention, $R^1$ is H, $C_{1-4}$ alkyl or $C_{2-4}$ alkenyl. In a further embodiment according to first aspect of the present invention, $R^1$ is hydrogen, n-propyl or 2,2-difluorovinyl.

In one embodiment according to first aspect of the present invention, $R^2$ is $C_{1-4}$ alkyl. In another embodiment according to first aspect of the present invention, $R^2$ is ethyl.

In one embodiment according to first aspect of the present invention, X is —$CONR^4R^5$, —COOH or —$COOR^3$, wherein $R^3$ is a $C_{1-4}$ alkyl. In another embodiment according to first aspect of the present invention, X is —$CONR^4R^5$.

In one embodiment according to first aspect of the present invention, X is —$CONR^4R^5$ or —$COOR^3$, wherein $R^3$ is a $C_{1-4}$ alkyl. In another embodiment according to first aspect of the present invention, X is $COOR^3$, wherein $R^3$ is a $C_{1-4}$ alkyl.

In one embodiment according to first aspect of the present invention, X is —$CONR^4R^5$ or —$COOR^3$, wherein $R^3$ is a $C_{1-4}$ alkyl. In another embodiment according to first aspect of the present invention, X is $COOR^3$, wherein $R^3$ is a $C_{1-4}$ alkyl.

In a particular embodiment, $R^3$ is methyl.

In one embodiment according to first aspect of the present invention, $R^4$ is hydrogen or $C_{1-4}$ alkyl. In another embodiment according to first aspect of the present invention, $R^4$ is hydrogen.

In one embodiment according to first aspect of the present invention, $R^5$ is hydrogen or $C_{1-4}$ alkyl. In another embodiment according to the first aspect of the present invention, $R^5$ is hydrogen.

Preferably $R^1$ is hydrogen, n-propyl or 2,2-difluorovinyl; $R^2$ is ethyl; and X is —$CONH_2$.

More preferably, the active ingredient is selected among Brivaracetam, Seletracetam and Levetiracetam. The best results have been obtained with Brivaracetam and Seletracetam.

Accordingly, the present invention relates to a pharmaceutical composition comprising a granulate which contains an active ingredient and which is coated with a controlled release layer. Usually, the weight percentage of the controlled release layer is comprised between 1.0% and 60%, relative to the weight of the pharmaceutical composition. Preferably, the weight percentage of the controlled release layer is comprised between 2.0% and 50%. More preferably, the weight percentage of the controlled release layer is comprised between 5.0% and 40%, relative to the weight of the pharmaceutical composition.

According to the invention, the controlled release layer comprises at least a controlled release polymer. By controlled release polymer, it is understood a polymer that could control the release rate of the active ingredient thanks to its solubility/permeability properties in an aqueous environment.

Generally, the controlled release polymer consists in ammonioalkyl methacrylate ethyl acrylate copolymers, or in ethylacrylate methyl methacrylate copolymer, or in ethylcellulose, or in cellulose acetate having a level of acetyl group comprised between 32% and 44%, or in a mix of thereof. Preferably, the controlled release polymer is chosen among a copolymer of ammonioalkyl methacrylate and ethyl acrylate, having an average molecular weight comprised between 75000 and 200.000 da, and having a level of ammonioalkyl methacrylate moieties comprised between 6% and 14%; or a copolymer of ethyl acrylate and methyl methacrylate in a molar ratio of 2:1 of the two monomers and having an average molecular weight comprised between 500000 and 1000000. Best results have been obtained with a copolymer of ammonioalkyl methacrylate and ethyl acrylate, sold under the trade name EUDRAGIT® RS or EUDRAGIT® RL and marketed by Evonik Industries AG; and with a copolymer of ethyl acrylate and methyl methacrylate sold under the trade name EUDRAGIT® NE 30 D and marketed by Evonik Industries AG, as a 30% aqueous dispersion.

Usually, the controlled release layer contains at least an excipient, such as co-binders, antisticking agents, antifoams, flavoring agents, pigment, processing aid agents, like plasticizers, emulsifier or stabilizer.

Generally the controlled release layer comprises a co-binder. Generally, the co-binder is chosen among cellulose derivatives, polyvinylalcohol or polyvinylpyrrolidone or a mixture thereof. Preferably, the co-binder is a cellulose derivative. More preferably it is hydroxypropylmethylcellulose (HPMC). The best results have been obtained with hydroxypropylmethylcellulose USP 28 designation type 2910 as co-binder.

Generally the controlled release layer comprises an antisticking agent. Generally, the antisticking agent is chosen among talc, colloidal silicon dioxide, magnesium trisilicate, starch, tribasic calcium phosphate, or a mixture thereof. Preferably, it is talc.

Usually, the pharmaceutical composition according to the present invention comprises 30 to 100% per weight of controlled release polymer with respect to the total dry mass of the controlled release layer. Preferably, the pharmaceutical composition according to the present invention comprises 40 to 90% per weight of controlled release polymer, more preferably 60 to 75% per weight of controlled release polymer with respect to the total dry mass of the controlled release layer.

Usually, the pharmaceutical composition according to the present invention comprises 0 to 15% per weight of co-binder with respect to the total dry mass of the controlled release layer. Preferably, the pharmaceutical composition according to the present invention comprises 1 to 10% per weight of co-binder, more preferably 3 to 5% per weight of co-binder with respect to the total dry mass of the controlled release layer.

Usually, the pharmaceutical composition according to the present invention comprises 0 to 50% per weight of the antisticking agent with respect to the total dry mass of the controlled release layer. Preferably, the pharmaceutical composition according to the present invention comprises 10 to 45% per weight of the antisticking agent, more preferably 25 to 35% per weight of the antisticking agent with respect to the dry mass of the controlled release layer.

Generally, the inert core is a sphere having a sphericity degree greater than 0.75 and having a density comprised between 0.5 and 1.5. Preferably, the inert core is a sphere having a sphericity degree comprised greater than 0.85 and having a density comprised between 0.6 and 1.2 Best results have been obtained with a sphere having a sphericity degree greater than 0.90, and having a density comprised between 0.80 and 0.90. By sphericity degree, it is understood the ratio of the surface area of a sphere (having the same volume as the given particle) to the surface area of the particle.

Generally, the inert core is neutral (i.e. it does not contain any active material).

Usually, the inert core is composed by sugar, saccharides, polysaccharides, cellulose, cellulose derivatives, microcrystalline cellulose, starch and/or waxes. Preferably the inert core comprises microcrystalline cellulose. More preferably, the inert core consists essentially in microcrystalline cellulose.

Generally, the average particle size of the inert core is between 75 and 1400 µm. Preferably, the average particle size of the inert core is between 400 and 1100 82 m. More preferably, the average particle size of the inert core is between 500 and 1000 µm. The best results have been obtained with neutral spheres of microcrystalline cellulose, sugar free, sold by Pharmatrans Sanaq AG under the trademark CELLETS® or sold by Asahi Kasei, under the trade name CELPHERE®; and, in particular, CELLETS®500, having an average particle size of 500-710 µm, CELLETS®700, having an average particle size of 700-1000 µm, CELPHERE® CP-507 having an average particle size of 500-710 µm and CELPHERE® CP-708 having an average particle size of 710-850 µm.

According to the invention, the first layer comprises an active ingredient and at least one excipient. Depending on the final dose, the level of the active layer could be varied.

Usually, the weight percentage of the first layer is comprised between 0.25% and 150%, relative to the weight of the inert core.

Preferably, the weight percentage of the first layer is comprised between 0.5% and 120%, relative to the weight of the inert core.

More preferably, the weight percentage of the first layer is comprised between 1.0% and 100%, relative to the weight of the inert core.

Usually, the excipient of the first layer comprises a binder.

Generally, the binder is chosen among cellulose derivatives, polyvinylalcohol, polyvinylpyrrolidone or a mixture thereof. Preferably, the binder is a cellulose derivative. More preferably, the binder is hydroxypropylmethylcellulose (HPMC). The best results have been obtained with hydroxypropylmethylcellulose USP 28 designation type 2910.

Usually, the excipient of the first layer comprises an antisticking agent. Generally, the antisticking agent is chosen among talc, colloidal silicon dioxide, magnesium trisilicate, starch, tribasic calcium phosphate, or a mixture thereof. Preferably, the antisticking agent is talc.

Preferably, the excipients of the first layer comprise hydroxylpropylmethyl-cellulose and talc.

Optionally, the excipient of the first layer comprises a preservative agent. Generally, the preservative agent is chosen among disodium edetate, sodium metabisulfite, ascorbic acid, butylated hydroxytoluene, citric acid or a mixture thereof. Preferably, the preservative agent is disodium edetate.

Usually, the pharmaceutical composition according to the present invention comprises 1 to 35% per weight of binder with respect to the total weight of the dry mass of the first layer. Preferably, the pharmaceutical composition according to the present invention comprises 2 to 25% per weight of binder, more preferably 5 to 15% per weight of binder with respect to the dry mass of the first layer.

Usually, the pharmaceutical composition according to the present invention comprises 0 to 40% per weight of the antisticking agent with respect to the dry mass of the first layer. Preferably, the pharmaceutical composition according to the present invention comprises 5 to 35% per weight of the antisticking agent, more preferably 10 to 30% per weight of the antisticking agent with respect to the dry mass of the first layer.

Usually, the pharmaceutical composition according to the present invention comprises 0 to 5% per weight of the preservative agent with respect to the dry mass of the first layer. Preferably, the pharmaceutical composition according to the present invention comprises 0 to 3% per weight of the preservative agent, more preferably 0 to 2% per weight of the preservative agent with respect to the dry mass of the first layer.

In another embodiment of the invention, an intermediate layer is added before the controlled release layer, in order to prevent any diffusion of the active ingredient into the controlled release layer, or to better protect the active ingredient against external chemical aggression. The granulate is coated with the intermediate layer. Generally, the intermediate layer comprises a binder, an anti-sticking agent, pigments, and/or processing aid agents like plasticizers.

Usually, the weight percentage of the intermediate layer is comprised between 1.0% and 30%, relative to the total weight of the inert core and the first layer.

Preferably, the weight percentage of the intermediate layer is comprised between 2.5% and 20%, relative to the total weight of the core and the first layer. More preferably, the weight percentage of the intermediate layer is comprised between 5% and 15%, relative to the total weight of the core and the first layer.

Usually, the intermediate coating layer comprises a binder. Generally, the binder is chosen among cellulose derivatives, polyvinylalcohol, polyvinylpyrrolidone, or a mixture therefore. Preferably, the binder is a cellulose derivative. More preferably it is hydroxypropylmethylcellulose (HPMC). The best results have been obtained with hydroxypropylmethylcellulose USP 28 designation type 2910.

Usually, the intermediate layer comprises an antisticking agent. Generally, the antisticking agent is chosen among talc, colloidal silicon dioxide, magnesium trisilicate, starch, tribasic calcium phosphate, or a mixture thereof. Preferably, it is talc.

Optionally, the intermediate layer comprises a plasticizer. Generally, the plasticizer is chosen among glycerol, fatty acids, phthalate, low molecular weight polyethylene glycol, citrate or a mixture thereof. Preferably it is polyethylene glycol.

By low molecular weight polyethylene glycol, it is understood polymer having a molecular weight lower than 12000 da.

Usually, the pharmaceutical composition according to the present invention comprises 30 to 95% per weight of binder with respect to the dry mass of the intermediate layer. Preferably, the pharmaceutical composition according to the present invention comprises 40 to 90% per weight of binder, more preferably 60 to 80% per weight of binder with respect to the dry mass of the intermediate layer.

Usually, the pharmaceutical composition according to the present invention comprises 0 to 40% per weight of the anti-sticking agent with respect to the dry mass of the intermediate layer. Preferably, the pharmaceutical composition according to the present invention comprises 5 to 35% per weight of the anti-sticking agent, more preferably 15 to 25% per weight of the anti-sticking agent with respect to the dry mass of the intermediate layer.

Usually, the pharmaceutical composition according to the present invention comprises 0 to 25% per weight of plasticizer with respect to the dry mass of the intermediate layer. Preferably, the pharmaceutical composition according to the present invention comprises 2 to 20% per weight of plasticizer, more preferably 6 to 10% per weight of plasticizer with respect to the dry mass of the intermediate layer.

In another embodiment of the invention, a final layer is added after the controlled release layer. The granulate coated with the controlled release layer is further coated with the final layer. The final layer comprises a binder, an antisticking agent, pigments, and/or processing aid agents.

Usually, the weight percentage of the final layer is comprised between 1.0% and 30%, relative to the total weight of the pharmaceutical composition. Preferably, the weight percentage of the final layer is comprised between 2.5% and 20%. More preferably, the weight percentage of the final layer is comprised between 5% and 15%, relative to the total weight of the pharmaceutical composition.

In another embodiment of the invention, an external phase is added. Several pharmaceutically acceptable excipients may be added to the composition, as external phase ingredient, such as pigment, preservatives or processing aid agents.

Examples of processing aid agents are talc, starches, stearic acid and anhydrous colloidal silica. Preferred processing aid agent according to the present invention is anhydrous colloidal silica, such as AEROSIL 200®.

Usually, the pharmaceutical composition according to the present invention comprises 0.0 to 3.0% per weight of processing aid agent. Preferably, the pharmaceutical composition according to the present invention comprises 0.0 to 2.0% per weight of processing aid agent, more preferably 0.25 to 1.0% per weight of processing aid agent with respect to the total weight of the composition.

According to the invention, optionally the composition also contains sweeteners, flavours, palatability agents.

In one embodiment of the invention, the pharmaceutical composition comprises
  a neutral core having an average particle size between 75 μm and 1400 μm;
  a first layer with a weight percentage, relative to the neutral core, between 0.25% and 150%, and containing Brivaracetam, as active ingredient, and 1 to 35% of binder, 0 to 40% of anti-sticking agent with respect to the total weight of the first layer;
  a controlled release layer with a weight percentage, relative to the total weight of the pharmaceutical composition, between 1.0 and 60%, and containing 30 to 100% of controlled release copolymer, 1 to 15% of binder, 0 to 50% of anti-sticking agent, respective to the total weight of the controlled release layer; and
  an external phase containing a processing aid agent at level of 0.0 to 3.0% respective to the total weight of the pharmaceutical composition.

Particularly, the present invention relates to a pharmaceutical composition comprising
  a neutral core having an average particle size between 400 μm and 1100 μm;
  a first layer with a weight percentage, relative to the neutral core, between 0.5% and 120%, and containing Brivaracetam, as active ingredient, and 2 to 25% of binder, 5 to 35% of antisticking agent with respect to the total weight of the first coating layer;
  a controlled release layer with a weight percentage, relative to the total weight of the pharmaceutical composition between 2.0 and 50%, and containing 40 to 90% of controlled release copolymer, 1 to 10% of binder, 10 to 45% of antisticking agent, respective to the total weight of the controlled release layer; and
  an external phase containing a processing aid agent at level of 0.0 to 2.0% respective to the total weight of the composition.

More particularly the present invention relates to a pharmaceutical composition comprising
  a neutral core having an average particle size between 500 μm and 1000 μm;
  a first layer with a weight percentage, relative to the neutral core, between 1.0% and 100%, and containing Brivaracetam, as active ingredient, and 5 to 15% of binder, 10 to 30% of antisticking agent, with respect to the total weight of the first coating layer;

a controlled release layer with a weight percentage, relative to the total weight of the pharmaceutical composition, between 5.0 and 40%, and containing 60 to 75% of controlled release copolymer, 3 to 5% of binder, 25 to 35% of antisticking agent, respective to the total weight of the controlled release layer; and an external phase containing a processing aid agent at level of 0.25 to 1.0% respective to the total weight of the composition.

In a particular embodiment, the present invention relates to a pharmaceutical composition comprising a neutral microcrystalline core having an average particle size between 75 μm and 1400 μm;

a first layer with a weight percentage, relative to the neutral core, between 0.25% and 150%, and containing Brivaracetam, as active ingredient, and 1 to 35% of hydroxyl-propylmethylcellulose, 0 to 40% of talc with respect to the total weight of the first coating layer;

a controlled release layer with a weight percentage, relative to the total weight of the pharmaceutical composition, between 1.0 and 60%, and containing 30 to 100% of ethylacrylate-methylmethacrylate copolymer, 1 to 15% of hydroxypropylmethyl-cellulose, 0 to 50% of talc, respective to the total weight of the controlled release layer; and an external phase containing colloidal anhydrous silica at level of 0.0 to 3.0% respective to the total weight of the composition.

In a particular embodiment, the present invention relates to a pharmaceutical composition comprising a neutral microcrystalline core having an average particle size between 400 μm and 1100 μm;

a first layer with a weight percentage, relative to the neutral core, between 0.5% and 120%, and containing Brivaracetam as active ingredient and 2 to 25% of hydroxyl-propylmethylcellulose, 5 to 35% of talc with respect to the total weight of the first coating layer;

a controlled release layer with a weight percentage, relative to the total weight of the pharmaceutical composition, between 2.0 and 50%, and containing 40 to 90% of ethylacrylate-methylmethacrylate copolymer, 1 to 10% of hydroxypropylmethyl-cellulose, and 10 to 45% of talc respective to the total weight of the controlled release layer and an external phase containing colloidal anhydrous silica at level of 0.0 to 2.0% respective to the total weight of the composition.

More particularly the present invention relates to a pharmaceutical composition comprising a neutral core having an average particle size between 500 μm and 1000 μm;

a first layer with a weight percentage, relative to the neutral core, between 1.0% and 100%, and containing Brivaracetam as active ingredient and 5 to 15% of hydroxyl-propylmethylcellulose, 10 to 30% of talc, with respect to the total weight of the first coating layer;

a controlled release layer with a weight percentage, relative to the total weight of the pharmaceutical composition, between 5.0 and 40%, and containing 60 to 75% of ethylacrylate-methylmethacrylate copolymer, 3 to 5% of hydroxypropylmethyl-cellulose, 25 to 35% of talc, respective to the total weight of the controlled release layer; and an external phase containing colloidal anhydrous silica at level of 0.25 to 1.0% respective to the total weight of the composition.

In another embodiment of the invention, the pharmaceutical composition comprises a neutral core having an average particle size between 75 μm and 1400 μm;

a first layer with a weight percentage, relative to the neutral core, between 0.25% and 150%, and containing Seletracetam as active ingredient and 1 to 35% of binder, 0 to 40% of antisticking agent with respect to the total weight of the first coating layer;

an intermediate layer with a weight percentage, relative to the total weight of the neutral core and of the first layer, between 1% and 30%, and containing 30 to 95% of binder, 0 to 40% of antisticking agent, 0 to 25% of plasticizer with respect to the total weight of the intermediate coating layer;

a controlled release layer with a weight percentage, relative to the total weight of the pharmaceutical composition, between 1.0 and 60%, and containing 30 to 100% of controlled release copolymer,1 to 15% of binder, 0 to 50% of antisticking agent respective to the total weight of the controlled release layer; and an external phase containing a processing aid agent at level of 0.0 to 3.0% respective to the total weight of the composition.

Particularly, the present invention relates to a pharmaceutical composition comprising a neutral core having an average particle size between 400 μm and 1100 μm;

a first layer with a weight percentage, relative to the neutral core, between 0.5% and 120%, and containing Seletracetam, as active ingredient, and 2 to 25% of binder, 5 to 35% of antisticking agent with respect to the total weight of the first coating layer;

an intermediate layer with a weight percentage, relative to the total weight of the neutral core and of the first layer, between 2.5% and 20%, and containing 40 to 90% of binder, 5 to 35% of antisticking agent, 2 to 20% of plasticizer with respect to the total weight of the intermediate coating layer;

a controlled release layer with a weight percentage, relative to the total weight of the pharmaceutical composition, between 2.0 and 50%, and containing 40 to 90% of controlled release copolymer, 1 to 10% of binder, and 10 to 45% of antisticking agent, respective to the total weight of the controlled release layer; and an external phase containing a processing aid agent at level of 0.0 to 2.0% respective to the total weight of the composition.

More particularly the present invention relates to a pharmaceutical composition comprising a neutral core having an average particle size between 500 μm and 1000 μm;

a first layer with a weight percentage, relative to the neutral core, between 1.0% and 100%, and containing Seletracetam, as active ingredient, and 5 to 15% of binder, 10 to 30% of antisticking agent with respect to the total weight of the first coating layer;

an intermediate layer with a weight percentage, relative to the total weight of the neutral core and of the first layer, between 5% and 15%, and containing 60 to 80% of binder, 15 to 25% of antisticking agent, 6 to 10% of plasticizer with respect to the total weight of the intermediate coating layer;

a controlled release layer with a weight percentage, relative to the total weight of the pharmaceutical composition, between 5.0 and 40%, and containing 60 to 75% of controlled release copolymer, 3 to 5% of binder, 25 to 35% of antisticking agent, respective to the total weight of the controlled release layer; and an external phase containing a processing aid agent at level of 0.25 to 1.0% respective to the total weight of the composition.

In a particular embodiment, the present invention relates to a pharmaceutical composition comprising a neutral microcrystalline core having an average particle size between 75 µm and 1400 µm;

a first layer with a weight percentage, relative to the neutral core, between 0.25% and 150%, and containing Seletracetam as active ingredient and 1 to 35% of hydroxyl-propylmethylcellulose, 0 to 40% of talc with respect to the total weight of the first coating layer;

an intermediate layer with a weight percentage, relative to the total weight of the neutral core and of the first layer, between 1.0% and 30%, and containing 30 to 95% of hydroxypropylmethylcellulose, 0 to 40% of talc, 0 to 25% of polyethylene glycol with respect to the total weight of the intermediate coating layer;

a controlled release layer with a weight percentage, relative to the total weight of the pharmaceutical composition, between 1.0 and 60%, and containing 30 to 100% of ethylacrylate-methylmethacrylate copolymer, 1 to 15% of hydroxypropylmethylcellulose, 0 to 50% of talc relative to the total weight of the controlled release layer, and colloidal anhydrous silica in the external phase at level of 0.0 to 3.0% respective to the total weight of the composition.

Particularly, the present invention relates to a pharmaceutical composition comprising a neutral microcrystalline core having an average particle size between 400 µm and 1100 µm;

a first layer with a weight percentage, relative to the neutral core, between 0.5% and 120%, and containing Seletracetam as active ingredient and 2 to 25% of hydroxypropylmethylcellulose, 5 to 35% of talc with respect to the total weight of the first coating layer;

an intermediate layer with a weight percentage, relative to the total weight of the neutral core and of the first layer, between 2.5% and 20%, and containing 40 to 90% of hydroxypropylmethylcellulose, 5 to 35% of talc, 2 to 20% of polyethylene glycol with respect to the total weight of the intermediate coating layer;

a controlled release layer with a weight percentage, relative to the total weight of the pharmaceutical composition, between 2.0 and 50%, and containing 40 to 90% of ethylacrylate-methylmethacrylate copolymer, 1 to 10% of hydroxypropylmethylcellulose, 10 to 45% of talc, respective to the total weight of the controlled release layer; and an external phase containing colloidal anhydrous silica at level of 0.0 to 2.0% respective to the total weight of the composition.

More particularly the present invention relates to a pharmaceutical composition comprising a neutral core having an average particle size between 500 µm and 1000 µm;

a first layer with a weight percentage, relative to the neutral core, between 1.0% and 100%, and containing Seletracetam as active ingredient and 5 to 15% of hydroxypropylmethylcellulose, 10 to 30% of talc with respect to the total weight of the first coating layer;

an intermediate layer with a weight percentage, relative to the total weight of the neutral core and of the first layer, between 5% and 15%, and containing 60 to 80% of hydroxypropylmethylcellulose, 15 to 25% of talc, 6 to 10% of polyethylene glycol with respect to the total weight of the intermediate coating layer;

a controlled release layer with a weight percentage, relative to the total weight of the pharmaceutical composition, between 5.0 and 40%, and containing 60 to 75% of ethylacrylate-methylmethacrylate copolymer, 3 to 5% of hydroxypropylmethyl-cellulose, 25 to 35% of talc, respective to the total weight of the controlled release layer; and an external phase containing colloidal anhydrous silica at level of 0.25 to 1.0% respective to the total weight of the composition.

In another embodiment of the invention, the pharmaceutical composition comprises a neutral core having an average particle size between 75 µm and 1400 µm;

a first layer with a weight percentage, relative to the neutral core, between 0.25% and 150%, and containing Levetiracetam, as active ingredient, and 1 to 35% of binder, 0 to 40% of anti-sticking agent with respect to the total weight of the first layer;

a controlled release layer with a weight percentage, relative to the total weight of the pharmaceutical composition, between 1.0 and 60%, and containing 30 to 100% of controlled release copolymer, 1 to 15% of binder, 0 to 50% of anti-sticking agent, respective to the total weight of the controlled release layer; and an external phase containing a processing aid agent at level of 0.0 to 3.0% respective to the total weight of the pharmaceutical composition.

Particularly, the present invention relates to a pharmaceutical composition comprising a neutral core having an average particle size between 400 µm and 1100 µm;

a first layer with a weight percentage, relative to the neutral core, between 0.5% and 120%, and containing Levetiracetam, as active ingredient, and 2 to 25% of binder, 5 to 35% of antisticking agent with respect to the total weight of the first coating layer;

a controlled release layer with a weight percentage, relative to the total weight of the pharmaceutical composition between 2.0 and 50%, and containing 40 to 90% of controlled release copolymer, 1 to 10% of binder, 10 to 45% of antisticking agent, respective to the total weight of the controlled release layer; and an external phase containing a processing aid agent at level of 0.0 to 2.0% respective to the total weight of the composition.

More particularly the present invention relates to a pharmaceutical composition comprising a neutral core having an average particle size between 500 µm and 1000 µm;

a first layer with a weight percentage, relative to the neutral core, between 1.0% and 100%, and containing Levetiracetam, as active ingredient, and 5 to 15% of binder, 10 to 30% of antisticking agent, with respect to the total weight of the first coating layer;

a controlled release layer with a weight percentage, relative to the total weight of the pharmaceutical composition, between 5.0 and 40%, and containing 60 to 75% of controlled release copolymer, 3 to 5% of binder, 25 to 35% of antisticking agent, respective to the total weight of the controlled release layer; and an external phase containing a processing aid agent at level of 0.25 to 1.0% respective to the total weight of the composition.

In a particular embodiment, the present invention relates to a pharmaceutical composition comprising
- a neutral microcrystalline core having an average particle size between 75 µm and 1400 µm;
- a first layer with a weight percentage, relative to the neutral core, between 0.25% and 150%, and containing Levetiracetam, as active ingredient, and 1 to 35% of hydroxyl-propylmethylcellulose, 0 to 40% of talc with respect to the total weight of the first coating layer;
- a controlled release layer with a weight percentage, relative to the total weight of the pharmaceutical composition, between 1.0 and 60%, and containing 30 to 100% of ethylacrylate-methylmethacrylate copolymer, 1 to 15% of hydroxypropylmethyl-cellulose, 0 to 50% of talc, respective to the total weight of the controlled release layer; and
- an external phase containing colloidal anhydrous silica at level of 0.0 to 3.0% respective to the total weight of the composition.

In a particular embodiment, the present invention relates to a pharmaceutical composition comprising
- a neutral microcrystalline core having an average particle size between 400 µm and 1100 µm;
- a first layer with a weight percentage, relative to the neutral core, between 0.5% and 120%, and containing Levetiracetam as active ingredient and 2 to 25% of hydroxyl-propylmethylcellulose, 5 to 35% of talc with respect to the total weight of the first coating layer;
- a controlled release layer with a weight percentage, relative to the total weight of the pharmaceutical composition, between 2.0 and 50%, and containing 40 to 90% of ethylacrylate-methylmethacrylate copolymer, 1 to 10% of hydroxypropylmethyl-cellulose, and 10 to 45% of talc respective to the total weight of the controlled release layer and
- an external phase containing colloidal anhydrous silica at level of 0.0 to 2.0% respective to the total weight of the composition.

More particularly the present invention relates to a pharmaceutical composition comprising
- a neutral core having an average particle size between 500 µm and 1000 µm;
- a first layer with a weight percentage, relative to the neutral core, between 1.0% and 100%, and containing Levetiracetam as active ingredient and 5 to 15% of hydroxyl-propylmethylcellulose, 10 to 30% of talc, with respect to the total weight of the first coating layer;
- a controlled release layer with a weight percentage, relative to the total weight of the pharmaceutical composition, between 5.0 and 40%, and containing 60 to 75% of ethylacrylate-methylmethacrylate copolymer, 3 to 5% of hydroxypropylmethyl-cellulose, 25 to 35% of talc, respective to the total weight of the controlled release layer; and
- an external phase containing colloidal anhydrous silica at level of 0.25 to 1.0% respective to the total weight of the composition.

The pharmaceutical composition of the invention can be manufactured by any process according to conventional methods known to the man skilled in the art, such as compression, extrusion, wet or dry granulation, by binding of powders, by means of spray processes, rotor granulation or fluidized bed granulation.

Optionally, the controlled release layer could require to be cured at a temperature comprised between 20° C. and 75° C., for a duration comprised between 1 h and 5 days. Preferably, the controlled release layer could require to be cured at a temperature comprised between 30° C. and 70° C., for a duration comprised between 2 h and 3 days. More preferably, the controlled release layer could require to be cured at a temperature comprised between 40° C. and 65° C., for a duration comprised between 8 h and 1 day.

In a further particular embodiment, the present invention relates to a pharmaceutical composition comprising 0.20 to 70% per weight of Brivaracetam, with respect to the total weight of the composition.

Usually, in this further particular embodiment, the present invention relates to a pharmaceutical composition comprising 0.40 to 60% per weight of Brivaracetam with respect to the total weight of the composition.

Particularly, in this further particular embodiment, the present invention relates to a pharmaceutical composition comprising 0.60 to 50% per weight of Brivaracetam with respect to the total weight of the composition.

The pharmaceutical composition according to the present invention is preferably administered orally.

The pharmaceutical composition according to the present invention is preferably administered in the form of a capsule, a sachet or a tablet.

Optionally, the pharmaceutical composition according to the present invention may contain an external diluent or a processing aid, such as (but not limited to) starch, lactose, microcrystalline cellulose, talc.

Optionally, the pharmaceutical composition according to the present invention may contain a sweetening agent such as sucrose or saccharine, a coloring agent or a flavoring agent.

Optionally, the pharmaceutical composition according to the present invention may comprise a taste-masking agent.

In another further particular embodiment, the present invention relates to a pharmaceutical composition comprising 0.20 to 70% per weight of Seletracetam, with respect to the total weight of the composition.

Usually, in this further particular embodiment, the present invention relates to a pharmaceutical composition comprising 0.40 to 60% per weight of Seletracetam with respect to the total weight of the composition.

Particularly, in this further particular embodiment, the present invention relates to a pharmaceutical composition comprising 0.60 to 50% per weight of Seletrecetam with respect to the total weight of the composition.

The pharmaceutical composition according to the present invention is preferably administered orally.

The pharmaceutical composition according to the present invention is preferably administered in the form of a capsule, a sachet or a tablet.

Optionally, the pharmaceutical composition according to the present invention contains an external diluent or a processing aid, such as (but not limited to) starch, lactose, microcrystalline cellulose, talc.

Optionally, the pharmaceutical composition according to the present invention contains a sweetening agent such as sucrose or saccharine, a coloring agent or a flavoring agent.

Optionally, the pharmaceutical composition according to the present invention comprises a taste-masking agent.

The present invention also concerns a use of a pharmaceutical composition for the treatment of disease.

In another aspect the present invention relates to a pharmaceutical composition comprising an active ingredient useful for the treatment or prevention of a disease.

By the term "disease", we understand a disease selected from the group consisting of epileptogenesis, seizure disorders, convulsions, Parkinson's disease, dyskinesia induced by dopamine replacement therapy, tardive dyskinesia induced by administration of neuroleptic drugs, Huntington Chorea, and other neurological disorders including bipolar disorders, mania, depression, anxiety, attention deficit hyperactivity disorder (ADHD), migraine, trigeminal and other neuralgia, chronic pain, neuropathic pain, cerebral ischemia, cardiac arrhythmia, myotonia, cocaine abuse, stroke, myoclonus, tremor, essential tremor, simple or complex tics, Tourette syndrome, restless leg syndrome and other movement disorders, neonatal cerebral haemorrhage, amyotrophic lateral sclerosis, spasticity and degenerative diseases.

The term "treatment" as used herein, includes curative treatment and prophylactic treatment.

By "curative" is meant efficacy in treating a current symptomatic episode of a disorder or condition.

By "prophylactic" is meant prevention of the occurrence or recurrence of a disorder or condition.

The present invention concerns also a method for treatment of a human patient by using the pharmaceutical composition.

The present invention concerns also the pharmaceutical composition for use as a medicament for curing the said disease.

The present invention concerns also the use of the pharmaceutical composition for the manufacture of a medicament for a therapeutic application in the said disease.

Preferably said disease is selected from the group consisting essentially of epilepsy, Parkinson's disease, dyskinesia, migraine, tremor, essential tremor, bipolar disorders, chronic pain, neuropathic pain. More preferably said disease is epilepsy.

The present invention concerns also a method for manufacturing a medicament intended for therapeutic application in the said disease, characterized in that the pharmaceutical composition according to the present invention is used.

A large dose range can be covered by varying the quantity of the pharmaceutical composition of the invention and the active ingredient load. Either immediate release (IR) or prolonged release (PR) behavior can be achieved, as IR compositions are preliminary to the PR compositions. Finally, the dissolution profile can be easily modulated by varying the thickness of the PR coating. Moreover, prolonged release multi-particulate forms generally offer an enhanced robustness and reliability on the release profile of the active ingredient.

The pharmaceutical composition of the invention releases at least 50% of the active ingredient in less than 8 hours in order to achieve acceptable drug absorption in vivo.

The following examples illustrate the invention without however limiting its scope.

EXAMPLE 1

Seletracetam Formulation

Low drug load pellets were prepared according to the composition given in Table 1.

TABLE 1

Core compositions of Seletracetam pellets with low drug load

| Step | | Material | Quantity |
| --- | --- | --- | --- |
| Step 1 | First layer | CELLET ® 700 | 98.5% |
| | | Seletracetam | 1.0% |
| | | Disodium edetate | 0.01% |
| | | PHARMACOAT ® 603 | 0.1% |
| | | Talc | 0.3% |

TABLE 1-continued

Core compositions of Seletracetam pellets with low drug load

| Step | | Material | Quantity |
| --- | --- | --- | --- |
| Step 2 | Intermediate layer | Pellets from step 1 | 90.9% |
| | | PHARMACOAT ® 603 | 6.4% |
| | | Talc | 1.9% |
| | | Polyethylene glycol 6000 | 0.7% |
| Step 3 | Controlled release coating | Pellets from step 2 | 89.3% |
| | | EUDRAGIT ® NE 30D | 7.2% |
| | | Talc | 3.1% |
| | | PHARMACOAT ® 606 | 0.4% |
| Step 4 | External process aid agent | Colloidal anhydrous silica | 0.50% relative to final pellets weight |
| Step 5 | Curing | Pellets from step 4 are placed at 60° C. for 24 h | |

Microcrystalline core pellets (MCC spheres) are sold under trade name CELLET®. The grade "700" refers to an average particle size ranging between 700 and 1000 µm. Hydropropyl methylcellulose (HPMC) sold under the trademark PHARMACOAT® is used as a binder agent. The grade 603 and 606 are preferred. Talc is an antisticking agent. Disodium edetate is used as a preservative agent. Polyethyleneglycol (PEG 6000) is a plasticiser of Hydropropyl methylcellulose. The grade "6000" is preferred for the application. It refers to an average molecular weight of 6000 da. Ethylacrylate-methylmethacrylate copolymer is sold under the trademark EUDRAGIT® NE 300. Anhydrous colloidal silica is sold under the trademark AEROSIL® 200. It is used as antisticking and gliding agent.

The obtained pellets show a sustained release profile for Seletracetam, what comply with the in vitro dissolution requirements.

TABLE 2

| | results in % | | |
| --- | --- | --- | --- |
| Time Hours | 1.00.00 | 4.00.00 | 16.00.00 |
| Low drug load pellets | 21 | 53 | 100 |

The in vitro dissolution profiles in water were determined according to the USP <711> (apparatus n°2, 50 rpm, aqueous medium 500 ml) over an interval of time of 16 h. The dissolution was conducted at 37° C. in a pH 6.4 phosphate buffer.

EXAMPLE 2

Seletracetam Formulation

Medium drug load pellets were prepared according to the composition given in Table 3.

TABLE 3

Core compositions of Seletracetam pellets with medium drug load

| Step | | Material | Quantity |
| --- | --- | --- | --- |
| Step 1 | First layer | CELLETS ® 700 | 90.2% |
| | | Seletracetam | 7.0% |
| | | Disodium edetate | 0.1% |
| | | PHARMACOAT ® 603 | 0.7% |
| | | Talc | 2.1% |

TABLE 3-continued

Core compositions of Seletracetam pellets with medium drug load

| Step | | Material | Quantity |
|---|---|---|---|
| Step 2 | Intermediate layer | Pellets from step 1 | 90.9% |
| | | PHARMACOAT ® 603 | 6.4% |
| | | Talc | 1.9% |
| | | Polyethylene glycol 6000 | 0.7% |
| Step 3 | Controlled release coating | Pellets from step 2 | 88.9% |
| | | EUDRAGIT ® NE 30D | 7.5% |
| | | Talc | 3.2% |
| | | PHARMACOAT ® 606 | 0.4% |
| Step 4 | External process aid agent | Colloidal anhydrous silica | 0.50% relative to final pellets weight |
| Step 5 | Curing | Pellets from step 4 are placed at 60° C. for 24 h | |

Microcrystalline core pellets are sold under trade name CELLET®. The grade 700 refers to a average particle size ranging between 700 and 1000 μm. Hydropropyl methylcellulose sold under the trademark PHARMACOAT® is used as a binder agent. The grade 603 and 606 are preferred. Talc is an antisticking agent. Disodium edetate is used as a preservative agent. Polyethyleneglycol (PEG 6000) is a plasticiser of hydropropyl methylcellulose. The grade "6000" is preferred for the application. It refers to an average molecular weight of 6000 da. Ethylacrylate-methylmethacrylate copolymer is sold under the trademark EUDRAGIT® NE 30D. Anhydrous colloidal silica is sold under the trademark AEROSIL® 200. It is used as antisticking and gliding agent.

The obtained pellets show a sustained release profile for Seletracetam, what comply with the in vitro dissolution requirements.

TABLE 4 results in %

| Time Hours | 1.00.00 | 4.00.00 | 16.00.00 |
|---|---|---|---|
| Medium drug load pellets | 27 | 63 | 101 |

The in vitro dissolution profiles in water were determined according to the USP <711> (apparatus n°2, 50 rpm, aqueous medium 900 ml) over an interval of time of 16 h. The dissolution was conducted at 37° C. in a pH 6.4 phosphate buffer.

EXAMPLE 3

Seletracetam Formulation

High drug load pellets were prepared according to the composition given in Table 5.

TABLE 5

Core compositions of Seletracetam pellets with high drug load

| Step | | Material | quantity |
|---|---|---|---|
| Step 1 | First layer | CELLETS ® 500 | 61.1% |
| | | Seletracetam | 27.5% |
| | | Disodium edetate | 0.4% |
| | | PHARMACOAT ® 603 | 2.8% |
| | | Talc | 8.3% |

TABLE 5-continued

Core compositions of Seletracetam pellets with high drug load

| Step | | Material | quantity |
|---|---|---|---|
| Step 2 | Intermediate layer | Pellets from step 1 | 90.9% |
| | | PHARMACOAT ® 603 | 6.4% |
| | | Talc | 1.9% |
| | | Polyethylene glycol 6000 | 0.7% |
| Step 3 | Controlled release coating | Pellets from step 2 | 81.3% |
| | | EUDRAGIT ® NE 30D | 12.5% |
| | | Talc | 5.4% |
| | | PHARMACOAT ® 606 | 0.8% |
| Step 4 | External process aid agent | Colloidal anhydrous silica | 0.50% relative to final pellets weight |
| Step 5 | Curing | Pellets from step 4 are placed at 60° C. for 24 h | |

Microcrystalline core pellets are sold under trade name CELLET®. The grade 500 refers to an average particle size ranging between 500 and 710 μm. Hydropropyl methylcellulose sold under the trademark PHARMACOAT® is used as a binder agent. The grade 603 and 606 are preferred. Talc is an antisticking agent. Disodium edetate is used as a preservative agent. Polyethyleneglycol (PEG 6000) is a plasticiser of hydropropyl methylcellulose. The grade "6000" is preferred for the application. It refers to an average molecular weight of 6000 da. Ethylacrylate-methylmethacrylate copolymer is sold under the trademark EUDRAGIT® NE 30D. Anhydrous colloidal silica is sold under the trademark AEROSIL® 200. It is used as antisticking and gliding agent.

The obtained pellets show a sustained release profile for Seletracetam, what comply with the in vitro dissolution requirements.

TABLE 6 results in %

| Time Hours | 1.00.00 | 4.00.00 | 16.00.00 |
|---|---|---|---|
| high drug load pellets | 16 | 65 | 100 |

The in vitro dissolution profiles in water were determined according to the USP <711> (apparatus n°2, 50 rpm, aqueous medium 900 ml) over an interval of time of 16 h. The dissolution was conducted at 37° C. in a pH 6.4 phosphate buffer.

EXAMPLE 4

Brivaracetam Sustained Release Formulation

Brivaracetam pellets were prepared according to the composition given in Table 7.

TABLE 7

Core compositions of Brivaracetam pellets

| Step | | Material | Quantity |
|---|---|---|---|
| Step 1 | Core First layer | CELLETS ® 700 | 72% |
| | | Brivaracetam | 20.0% |
| | | PHARMACOAT ® 603 | 2.0% |
| | | Talc | 6.0% |

TABLE 7-continued

Core compositions of Brivaracetam pellets

| Step | | Material | Quantity |
|---|---|---|---|
| Step 2 | Controlled release coating | Pellets from step 2 | 83.3% |
| | | EUDRAGIT ® NE 30D | 11.2% |
| | | Talc | 4.8% |
| | | PHARMACOAT ® 606 | 0.7% |
| Step 3 | External process aid agent | Colloidal anhydrous silica | 0.50% relative to final pellets weight |
| Step 4 | Curing | Pellets from step 3 are placed at 50° C. for 24 h | |

Microcrystalline core pellets are sold under trade name CELLET®. The grade 700 refers to an average particle size ranging between 700 and 1000 μm. Hydropropyl methylcellulose sold under the trademark PHARMACOAT® is used as a binder agent. The grade 603 and 606 are preferred. Talc is an antisticking agent. Ethylacrylate-methylmethacrylate copolymer is sold under the trademark EUDRAGIT® NE 30D. Anhydrous colloidal silica is sold under the trademark AEROSIL® 200. It is used as antisticking and gliding agent.

The obtained pellets show a sustained release profile for Brivaracetam what comply with the in vitro dissolution requirements.

TABLE 8

| | results in % | | |
|---|---|---|---|
| Time Hours | 1.00.00 | 4.00.00 | 16.00.00 |
| Brivaracetam pellets | 38 | 77 | 95 |

The in vitro dissolution profiles in water were determined according to the USP <711> (apparatus n°2, 50 rpm, aqueous medium 900 ml) over an interval of time of 16 h. The dissolution was conducted at 37° C. in a pH 6.4 phosphate buffer.

EXAMPLE 5

Levetiracetam

Levetiracetam pellets were prepared according to the composition given in Table 9.

TABLE 9

Core compositions of Levetiracetam pellets

| Step | | Material | quantity |
|---|---|---|---|
| | Core | CELLETS ® 700 | 72% |
| Step 1 | First layer | Levetiracetam | 20.0% |
| | | PHARMACOAT ® 603 | 2.0% |
| | | Talc | 6.0% |
| Step 2 | Controlled release coating | Pellets from step 2 | 80% |
| | | EUDRAGIT ® NE 30D | 13.9%% |
| | | Talc | 5.4%% |
| | | PHARMACOAT ® 606 | 0.7%% |
| Step 3 | External process aid agent | Colloidal anhydrous silica | 0.50% relative to final pellets weight |
| Step 4 | Curing | Pellets from step 3 are placed at 50° C. for 24 h | |

Microcrystalline core pellets are sold under trade name CELLET®. The grade 700 refers to an average particle size ranging between 700 and 1000 μm. Hydropropyl methylcellulose sold under the trademark PHARMACOAT® is used as a binder agent. The grade 603 and 606 are preferred. Talc is an antisticking agent. Ethylacrylate-methylmethacrylate copolymer is sold under the trademarkEUDRAGIT® NE 30D. Anhydrous colloidal silica is sold under the trademark AEROSIL® 200. It is used as antisticking and gliding agent.

The obtained pellets show a sustained release profile for Levetiracetam what comply with the in vitro dissolution requirements.

TABLE 10

| | results in % | | |
|---|---|---|---|
| Time Hours | 1.00.00 | 4.00.00 | 16.00.00 |
| Levetiracetam pellets | 1% | 28% | 99% |

The in vitro dissolution profiles in water were determined according to the USP <711> (apparatus n°2, 50 rpm, aqueous medium 900 ml) over an interval of time of 16 h. The dissolution was conducted at 37° C. in a pH 6.4 phosphate buffer.

EXAMPLE 6

Pharmacological data—: All experiments were performed in accordance with the Guidelines of the local Ethical Committee for Animal Experimentation.

Epileptiform responses in hippocampal slices: Levetiracetam reduces epileptiform responses induced in rat hippocampal slices by high-K+/low-Ca2+ concentrations in the perfusion fluid and induced by bicuculline. The effect of brivaracetam on epileptiform responses induced by high-K+/low-Ca2+ concentrations or by bicuculline was examined in transverse hippocampal slices prepared from Sprague-Dawley rats according to previously reported standard procedures. The epileptiform responses were induced by passing from a normal perfusion of artificial cerebrospinal fluid (ACSF) (K+3 mM; Ca2+2.4 mM) to either high-K+/low-Ca2+ fluid (HKLCF) (K+7.5 mM; Ca2+0.5 mM) or to 5 M bicuculline methiodide (BMI)-containing ACSF.

Extracellular field potentials (FPs) were recorded in the CA3 area of the slices with 2 M NaCl-filled glass microelectrodes. The evoked FPs were recorded at 10-min intervals in response to fimbrial stimulation with constant current rectangular pulses that elicit a single population spike (PS) of 50-75% of the maximal amplitude when the slice is in ACSF. In the HKLCF model, 2 min of spontaneous activity were also recorded, in the middle of each 10-min interval between the recordings of evoked responses.

Either brivaracetam or levetiracetam was added to the bathing fluid of the slices 20 min before shifting from ACSF to either HKLCF or 5 M BMI-containing ACSF, and was kept in the perfusion fluid throughout the experiment.

Audiogenic seizures in mice: Genetically sound-sensitive male mice (16-28 g; n=10 per group), responding with wild running, clonic and tonic convulsions to an acoustic stimulation, were used. Audiogenic seizures were induced by an acoustic stimulus (90 dB, 10-20 kHz) applied for 30 s. The mice were pretreated with either saline, brivaracetam (i.p., 30 min) or levetiracetam (i.p., 60 min), and the proportion of mice protected against clonic convulsions was used as the end point to assess anticonvulsant activity.

Chemically induced seizures in mice: Pentylenetetrazol, 83 mg kg–1 s.c., was used to evaluate the anticonvulsant properties of brivaracetam. The dose was selected based on dose-effect curves in saline-treated animals as the convulsive dose inducing clonic convulsions of all four extremities in 97% of the animals. Immediately after administration of the chemoconvulsant, the mice were placed individually in small plastic cages (25 13 8 cm) and observed for the presence of clonic convulsions in all four extremities, for 60 min. The occurrence of tonic convulsions (hindlimb extension) and mortality was also recorded during this interval. The proportion of mice protected against clonic convulsions was calculated and used as the end point for anticonvulsant activity.

Results

Epileptiform responses in hippocampal slices: Changing the perfusion of rat hippocampal slices from the normal ACSF to HKLCF produced increasingly epileptiform FPs in the CA3 area in response to constant-current fimbrial stimulation. In control slices exposed to HKLCF alone, the PS1 amplitude progressively increased, reaching plateau values within 20 min (4.250.77 mV), nearly twofold higher than those recorded under ACSF perfusion (2.180.15 mV; means.d. for n=10 slices). Also, constant-current single stimuli-evoked bursts of repetitive PSs (that is, PS2, PS3 and so on) increased markedly in number in the first 30 min of HKLCF perfusion from the single PS1 to an average of 7.62.3 PS per evoked burst, and continued to increase slightly up to the end of the records, reaching an average of 8.81.6 PS per evoked burst after 80-min perfusion of HKLCF. Both brivaracetam and levetiracetam reduced these epileptiform responses. Upon 15-min perfusion of HKLCF, spontaneous field bursts occurred in 4 out of the 10 control slices exposed to HKLCF alone, whereas from 25 min in HKLCF to the end of the records, all control slices presented regular field bursting. Brivaracetam (3.2 M), but not levetiracetam (32 M), reduced the rate of this spontaneous bursting.

In vivo studies: In fully amygdala-kindled rats, brivaracetam induced a significant suppression in motor-seizure severity from a dose of 21.2 mg kg–1, whereas levetiracetam induced a similar effect from a dose of 170 mg kg–1. Brivaracetam also significantly reduced the after-discharge duration at the highest dose tested (212.3 mg kg–1), whereas levetiracetam was inactive on this parameter up to 1700 mg kg–1.

Audiogenic seizure-susceptible mice were protected against the expression of clonic convulsions by brivaracetam and levetiracetam; ED50 values are shown in Table 2. Brivaracetam, administered i.p. 30 min before seizure induction in mice, also protected against clonic convulsions induced by pentylenetetrazol and against tonic hindlimb extension induced by a maximal electroshock in mice, although with higher ED50 values.

Brivaracetam significantly suppressed spontaneous SWDs in GAERS rats from a dose of 2.1 mg kg–1 with complete inhibition appearing at the highest dose tested (67.9 mg kg–1). Levetiracetam, on the other hand, induced significant suppression of SWDs from a dose of 5.4 mg kg–1.

Pretreatment with brivaracetam during corneal kindling of mice resulted in a significant reduction in the incidence of generalized motor seizures, and a similar incidence reduction was observed with levetiracetam at higher doses. Continued corneal stimulations following termination of treatment showed a persistent reduction in the incidence of generalized motor seizures in the group previously treated with the highest dose of brivaracetam.

The invention claimed is:

1. A sustained release pharmaceutical composition comprising a granulate wherein the granulate consists of
   (a) an inert core,
   (b) a first layer coating the inert core,
   (c) optionally, an intermediate layer coating the first layer, and
   (d) a controlled release layer coating the first layer or, when the intermediate layer is present, the intermediate layer,
   wherein
   (i) the active ingredient is brivaracetam or seletracetam,
   (ii) the controlled release layer consists of a controlled release polymer and, optionally, one or more excipients selected from the group consisting of co-binders, anti-sticking agents, antifoaming agents, flavoring agents, pigments, processing aid agents, emulsifiers, and stabilizers,
   (iii) the controlled release polymer is selected from the group consisting of ammonioalkyl methacrylate ethyl acrylate copolymers, ethylacrylate methyl methacrylate copolymer, ethylcellulose, a cellulose acetate having a level of acetyl group comprised between 32% and 44%, or a combination thereof,
   (iv) the co-binder, when present, is selected from the group consisting of hydroxyproplymethylcellulose, polyvinylalcohol, and polyvinylpyrrolidone,
   (v) the intermediate layer comprises a binder, an anti-sticking agent, pigments, and/or processing aid agents like plasticizers, and
   (vi) the first layer comprises an active ingredient and at least one excipient.

2. The pharmaceutical composition according to claim 1, wherein the weight percentage of the controlled release layer is between 1.0% and 60%, relative to the weight of the pharmaceutical composition.

3. The pharmaceutical composition according to claim 1, wherein the controlled release polymer is an ammonioalkyl methacrylate ethyl acrylate copolymer, a ethylacrylate methyl methacrylate copolymer, ethylcellulose, a cellulose acetate having a level of acetyl group of between 32% and 44%, or a combination thereof.

4. The pharmaceutical composition according to claim 3, wherein the controlled release polymer is a ammonioalkyl methacrylate and ethyl acrylate copolymer having an average molecular weight of between 75000 and 200000 da, and having a level of ammonioalkyl methacrylate moieties of between 6% and 14%; or a ethyl acrylate and methyl methacrylate copolymer with a molar ratio of 2:1 of the two monomers and an average molecular weight of between 500000 and 1000000.

5. The pharmaceutical composition according to claim 1, wherein the inert core is a sphere having a sphericity degree greater than 0.75 and having a density of between 0.5 and 1.5.

6. The pharmaceutical composition according to claim 1, wherein the inert core consists essentially of microcrystalline cellulose.

7. The pharmaceutical composition according to claim 1, wherein the average particle size of the inert core is between 75 and 1400 μm.

8. The pharmaceutical composition according to claim 1, wherein the first layer comprises the excipients hydroxylpropylmethylcellulose and talc.

9. The sustained release pharmaceutical composition according to claim 1, wherein the granulate is coated with an intermediate layer between the first layer and the controlled release layer.

10. A sustained release pharmaceutical composition comprising a granulate, wherein the granulate consists of
(a) an inert core,
(b) a first layer coating the inert core,
(c) optionally, an intermediate layer coating the first layer,
(d) a controlled release layer coating the first layer or, when the intermediate layer is present, the intermediate layer, and
(e) a final layer coating the controlled release layer,
wherein
(i) the active ingredient is brivaracetam or seletracetam,
(ii) the controlled release layer consists of a controlled release polymer and, optionally, one or more excipients selected from the group consisting of co-binders, antisticking agents, antifoaming agents, flavoring agents, pigments, processing aid agents, emulsifiers, and stabilizers,
(iii) the controlled release polymer is selected from the group consisting of ammonioalkyl methacrylate ethyl acrylate copolymers, ethylacrylate methyl methacrylate copolymer, ethylcellulose, a cellulose acetate having a level of acetyl group comprised between 32% and 44%, or a combination thereof,
(iv) the co-binder, when present, is selected from the group consisting of hydroxyproplymethylcellulose, polyvinylalcohol, and polyvinylpyrrolidone,
(v) the intermediate layer comprises a binder, an antisticking agent, pigments, and/or processing aid agents like plasticizers,
(vi) the first layer comprises an active ingredient and at least one excipient, and
(vii) the final layer consists essentially of a binder, an antisticking agent, a pigment, and/or a processing aid agent.

11. A sustained release pharmaceutical composition comprising a granulate, wherein the granulate consists of
(a) an inert core,
(b) a first layer coating the inert core,
(c) optionally, an intermediate layer coating the first layer,
(d) a controlled release layer coating the first layer or, when the intermediate layer is present, the intermediate layer, and
(e) an external phase,
wherein
(i) the active ingredient is brivaracetam or seletracetam,
(ii) the controlled release layer consists of a controlled release polymer and, optionally, one or more excipients selected from the group consisting of co-binders, antisticking agents, antifoaming agents, flavoring agents, pigments, processing aid agents, emulsifiers, and stabilizers,
(iii) the controlled release polymer is selected from the group consisting of ammonioalkyl methacrylate ethyl acrylate copolymers, ethylacrylate methyl methacrylate copolymer, ethylcellulose, a cellulose acetate having a level of acetyl group comprised between 32% and 44%, or a combination thereof,
(iv) the co-binder, when present, is selected from the group consisting of hydroxyproplymethylcellulose, polyvinylalcohol, and polyvinylpyrrolidone,
(v) the intermediate layer comprises a binder, an antisticking agent, pigments, and/or processing aid agents like plasticizers,
(vi) the first layer comprises an active ingredient and at least one excipient, and
(vii) the external phase consists essentially of one or more agents selected from pigments, preservatives, and processing aid agents.

12. The pharmaceutical composition according to claim 10, wherein the weight percentage of the controlled release layer is between 1.0% and 60%, relative to the weight of the pharmaceutical composition.

13. The pharmaceutical composition according to claim 10, wherein the controlled release polymer is a copolymer of ammonioalkyl methacrylate and ethyl acrylate, having an average molecular weight comprised between 75000 and 200000 da, and having a level of ammonioalkyl methacrylate moieties of between 6% and 14%; or a copolymer of ethyl acrylate and methyl methacrylate in a molar ratio of 2:1 of the two monomers and having an average molecular weight of between 500000 and 1000000.

14. The pharmaceutical composition according to claim 10, wherein the inert core is a sphere having a sphericity degree greater than 0.75 and having a density of between 0.5 and 1.5.

15. The pharmaceutical composition according to claim 10, wherein the inert core consists essentially of microcrystalline cellulose.

16. The pharmaceutical composition according to claim 10, wherein the average particle size of the inert core is between 75 and 1400 μm.

17. The pharmaceutical composition according to claim 10, wherein the excipients of the first layer comprise hydroxylpropylmethylcellulose and talc.

18. The pharmaceutical composition according to claim 10 wherein the amount of Brivaracetam or Seletracetam released in an in vitro 500 ml aqueous phosphate buffered medium at pH 6.4, at 50 rpm with United States Pharmacopeia Apparatus 2 over 16 hours at 37° C. is no more than 40% after 1 hour of dissolution, 25%-80% after 4 hours of dissolution, and no less than 80% after 16 hours of dissolution.

19. The pharmaceutical composition according to claim 10 wherein the amount of Brivaracetam or Seletracetam released in an in vitro 500 ml aqueous phosphate buffered medium at pH 6.4, at 50 rpm with United States Pharmacopeia Apparatus 2 over 16 hours at 37° C. is no more than 30% after 1 hour of dissolution, 45%-70% after 4 hours of dissolution, and no less than 80% after 16 hours of dissolution.

20. The pharmaceutical composition according to claim 9 wherein the amount of Brivaracetam or Seletracetam released in an in vitro 500 ml aqueous phosphate buffered medium at pH 6.4, at 50 rpm with United States Pharmacopeia Apparatus 2 over 16 hours at 37° C. is no more than 40% after 1 hour of dissolution, 25%-80% after 4 hours of dissolution, and no less than 80% after 16 hours of dissolution.

21. The pharmaceutical composition according to claim 9 wherein the amount of Brivaracetam or Seletracetam released in an in vitro 500 ml aqueous phosphate buffered medium at pH 6.4, at 50 rpm with United States Pharmacopeia Apparatus 2 over 16 hours at 37° C. is no more than 30% after 1 hour of dissolution, 45%-70% after 4 hours of dissolution, and no less than 80% after 16 hours of dissolution.

22. The pharmaceutical composition according to claim 11 wherein the amount of Brivaracetam or Seletracetam released in an in vitro 500 ml aqueous phosphate buffered medium at pH 6.4, at 50 rpm with United States Pharmacopeia Apparatus 2 over 16 hours at 37° C. is no more than 40% after 1 hour of dissolution, 25%-80% after 4 hours of dissolution, and no less than 80% after 16 hours of dissolution.

23. The pharmaceutical composition according to claim 11 wherein the amount of Brivaracetam or Seletracetam released in an in vitro 500 ml aqueous phosphate buffered medium at pH 6.4, at 50 rpm with United States Pharmacopeia Apparatus 2 over 16 hours at 37° C. is no more than 30% after 1 hour of dissolution, 45%-70% after 4 hours of dissolution, and no less than 80% after 16 hours of dissolution.

* * * * *